US008329225B2

(12) United States Patent
Muzykantov et al.

(10) Patent No.: US 8,329,225 B2
(45) Date of Patent: *Dec. 11, 2012

(54) ANTIOXIDANT POLYMER NANOCARRIERS FOR USE IN PREVENTING OXIDATIVE INJURY

(75) Inventors: Vladimir R. Muzykantov, Warwick, PA (US); Thomas D. Dziubla, Lexington, KY (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 752 days.

This patent is subject to a terminal disclaimer.

(21) Appl. No.: 12/481,876

(22) Filed: Jun. 10, 2009

(65) Prior Publication Data
US 2009/0258078 A1 Oct. 15, 2009

Related U.S. Application Data

(60) Division of application No. 11/266,785, filed on Nov. 4, 2005, now Pat. No. 7,597,907, which is a continuation of application No. 60/625,727, filed on Nov. 5, 2004.

(51) Int. Cl.
A61K 9/16 (2006.01)
A61K 9/50 (2006.01)
A61K 38/44 (2006.01)

(52) U.S. Cl. ........ 424/497; 424/94.4; 424/490; 424/499
(58) Field of Classification Search .................. 424/93.7, 424/94.4, 490, 497, 499
See application file for complete search history.

(56) References Cited

U.S. PATENT DOCUMENTS

| 5,543,158 | A | 8/1996 | Gref et al. |
| 5,866,540 | A | 2/1999 | Jonczyk et al. |
| 6,007,845 | A | 12/1999 | Domb et al. |
| 7,597,907 | B2 | 10/2009 | Muzykantov |
| 7,927,629 | B2 | 4/2011 | Simone |
| 2004/0001872 | A1 | 1/2004 | Shih et al. |
| 2004/0208929 | A1 | 10/2004 | Costantino |
| 2006/0073333 | A1 | 4/2006 | Anderson |
| 2006/0127386 | A1 | 6/2006 | Muzykantov |
| 2009/0110741 | A1 | 4/2009 | Simone et al. |
| 2010/0316571 | A1 | 12/2010 | Simone |

FOREIGN PATENT DOCUMENTS
WO WO-98/32466 7/1998

OTHER PUBLICATIONS

Li, PEGylated PLGA nanoparticles as protein carriers: synthesis, preparation and biodistribution in rats, J. Controlled Release, 71:203-211 (2001).
Office Action dated Jan. 26, 2010 from U.S. Appl. No. 11/925,834.
Amendment dated Apr. 7, 2010 from U.S. Appl. No. 11/925,834.
Atochina, et al., "Immunotargeting of catalase to ACE or ICAM-1 protects perfused rat lungs against oxidative stress", American J. Physiology, Lung Cellular and Molecular Physiology, 275(4 pt 1):L806-L817 (Oct. 1998).
Avgoustakis, et al., "PGLA-mPEG particles of cisplatin; in vitro nanoparticle degredation, in vitro drug release and in vitro drug residence in blood properties", J. Controlled Release, 79:123-135 (Feb. 19, 2002).
Christofidou-Solomidou, et al., "PECAM-directed delivery of catalase to endothelium protects against pulmonary vascular oxidative stress", American J. Physiology, Lung Cellular and Molecular Physiology, 285(2):L283-L292 (Aug. 2003).
Hansen, et al. "Attachment of antibodies to sterically stablized liposomes: evaluation, comparison and optimization of coupling procedures", Biochimica et Biophysica Acta, 1239:133-144 (Nov. 1, 1995).
Kozower, et al., "Immunotargeting catalase to the pulmonary endothelium alleviates oxidative stress and reduces acute lung transplantation injury" Nature Biotechnology, 21(4):392-398 (Apr. 2003; e-pub Mar. 24, 2003).
McCord, J.M., "Superoxide dismutase on aging and disease: an overview", Methods in Enzymology, 349:331-341 (2002).
Muro, et al., "Slow intracellular trafficking of catalase nanoparticles targeted to ICAM-1 protects endothelial cells from oxidative stress" American J. Physiology, Lung Cellular and Molecular Physiology, 285(5):C1339-C1347 (Nov. 2003 ; e-pub Jul. 23, 2003).
Muzykantov, et al, "Streptavidin facilitates internalization and pulmonary targeting of an anti-endothelial cell antibody (plateletendothelial cell adhesion molecule 1): A Strategy for vascular immunotargeting of drugs", Proceedings of the National Academy of Sciences USA, 96(5):2379-2384 (Mar. 1999).
Sweitzer, et al., "PECAM directed immunotargeting of catalase: specific, rapid and transient protection against hydrogen peroxide", Free Radical Biology & Medicine, 34(8):1035-1046 (Apr. 15, 2003).
Wiewrodt, et al., "Size-dependent intracellular immunotargeting of therapeutic cargoes into endothelial cells", Hemostasis, Thrombosis, and Vascular Biology, 99(3):912-922 (Feb. 1, 2002).
Zambaux, et al., "Protein-C loaded monomethoxypoly (ethylene oxide)-poly(lactic acid) nanoparticles", Int'l. J. Pharmaceutics, 212:1-9 (Jan. 5, 2001).
Muzykantov, V. R., "Targeting of superoxide dismutase and catalase to vascular endothelium", J. Control Release, 71(1): 1-21 (Mar. 12, 2001).
Langer, R., "Drug Delivery and Targeting", Nature, 392(6679 Suppl):5-10 (Apr. 30, 1998).
Moghimi, et al., "Stealth Liposomes and Long Circulating Nanoparticles: Critical issues in pharmacokinetics, opsonization and protein-binding properties", Progress in Lipid Research, 42(6):463-478 (Nov. 2003).

(Continued)

Primary Examiner — Jon P Weber
Assistant Examiner — Kailash C Srivastava
(74) Attorney, Agent, or Firm — Howson & Howson LLP

(57) ABSTRACT

The present invention is a method for encapsulating active protein in a polymeric nanocarrier. The instant method employs homogenization at subzero temperatures so that enzyme activity is retained. Enzymes which can be encapsulated by the present method include, for example, antioxidant enzymes and xenobiotic detoxifying enzymes. Encapsulation of an enzyme protects it from protease degradation and increases therapeutic half-life. Advantageously, polymeric nanoparticles of the invention are permeable to enzyme substrates and therefore enzymes encapsulated by the instant method can exert their effect without release from the nanocarrier. Methods for decomposing a reactive oxygen species, protecting against vascular oxidative stress, and detoxifying a xenobiotic are also provided.

23 Claims, No Drawings

OTHER PUBLICATIONS

Roux, et al., "On the characterization of pH sensitive liposome/polymer complexes", Biomacromolecules, 4(2):240-248 (Mar.-Apr. 2003).

Lasic, D. D., "Doxorubicin in sterically stabilized lysosomes", Nature, 380(6574):561 (Apr. 11, 1996).

Discher, et al, "Polymer vesicles", Science, 297(5583):967-973 (Aug. 9, 2002).

Zhang, et al., Micellization Phenomena of Amphiphilic Block Copolymers Based on Methoxy Poly(ethylene glycol) and Either Crystalline or Amorphous Poly(caprolactone-b-lactide), Biomacromolecules, 7(9):2492-2500 (Sep. 2006).

Vinogradov, et al., "Self-Assembly of Polyamine-Poly(ethylene glycol) Copolymers with Phosphorothioate Oligonucleotides" Bioconjugate Chemistry, 9(6):805-812 (Nov.-Dec. 1998).

Ravenelle, et al., "Self-Assembly of Poly([R]-3-hydroxybutyric acid)-Block-Poly(ethylene glycol) Diblock Copolymers" Biomacromolecules, 4(3):856-858 (May-Jun. 2003).

Zhang, et al., "Multiple morphologies of "crew cut" aggregates of polystyrene-b-poly(acrylic acid) block copolymers", Science, 268(5218):1728-1731 (Jun. 23, 1995).

Alakhov, et al., "Block copolymeric transport carriers as versatile vehicles for drug delivery", Expert Opinions on Investigational Drugs, 7(9):1453-1473 (Sep. 1998).

Dziubla, et al., "Polymer nanocarriers protecting enzyme cargo against proteolysis", J. Control Release, 102(2):427-439 (Feb. 2, 2005 ; e-pub Nov. 19, 2004).

Champion, et al., "Role of target geometry in phagocytosis" Proceedings of the National Academy of Sciences USA., 103(13):4930-4934 (Mar. 28, 2006 ; e-pub Mar. 20, 2006).

Son, et al., "Template synthesis of multifunctional nanotubes for controlled release" J. Control Release, 114(2):143-152 (Aug. 28, 2006 ; e-pub Jun. 7, 2006).

Cai, et al., "Micelles of different morphology: advantages of worm-like filomicelles of PEO-PCL is paclitaxel delivery" Pharmaceutical Research, 24:2009-2109 (Nov. 2007 ; e-pub Jun. 13, 2007).

Geng, et al., "Shape effects of filaments versus spherical particles in flow and drug delivery" Nature Nanotechnology, 2(4):249-255 (Mar. 25, 2007).

Geng, et al., "Visualization of degradable worm micelle breakdown in relation to drug release" Polymer, 47(7):2519-2525 (Feb. 7, 2006).

Shuvaev , et al., "Factors modulating the delivery and effect of enzymatic cargo conjugated with antibodies targeted to the pulmonary endothelium", J. Controlled Release, 118(2):235-244 (Apr. 2, 2007 ; e-pub Jan. 8, 2007).

Von Burkersroda, et al., "Why degradable polymers undergo surface erosion or bulk erosion", Biomaterials, 23(21):4221-4231 (Nov. 2002).

Gopferich, A., "Polymer Bulk Erosion" Macromolecules, 30(9):2598-2604 (Apr. 1, 1997).

Simone, et al., "Effect of Polymer Amphiphilicity on Loading of a Therapeutic Enzyme into Protective Filamentous and Spherical Polymer Nanocarriers", Biomacromolecules, 8(12):3914-3921 (Dec. 2007 ; e-pub Nov. 27, 2007).

Dziubla, et al., "Endothelial targeting of semi-permeable polymer nanocarriers for enzyme therapies" Biomaterials, 29(2):215-227 (Jan. 2008 ; e-pub Oct. 24, 2007).

Wu, et al., "Neuroprotection with noninvasive neurotrophin deliver to the brain", Proceedings of the National Academy of Sciences USA, 96:254-259 (Jan. 5, 1999).

Garnacho, et al., "Delivery of acid sphingomyelinase in normal and Niemann-Pick disease mice using ICAM-1-targeted polymer nanocarriers", J. Pharmacology and Experimental Therapeutics (e-pub Feb. 20, 2008).

Muzykantov, et al., "Immunotargeting of antioxidant enxymes to the pulmonary endothelium", Proceedings of the National Academy of Sciences USA, 96(5):5213-5218 (May 1996).

Office Action dated Jun. 28, 2010 issued in related U.S. Appl. No. 11/925,834.

Applicants' response filed Oct. 28, 2010 to Office Action dated Jun. 28, 2010 issued in related U.S. Appl. No. 11/925,834.

ANTIOXIDANT POLYMER NANOCARRIERS FOR USE IN PREVENTING OXIDATIVE INJURY

INTRODUCTION

This application is a divisional of U.S. patent application Ser. No. 11/266,785, filed Nov. 4, 2005 now U.S. Pat. No. 7,597,907 B2 which claims the benefit of priority of U.S. Provisional Patent Application Ser. No. 60/625,727, filed on Nov. 5, 2004, which are incorporated herein in their entirety by reference.

This invention was made in the course of research sponsored by the National Institutes of Health (NIH Grant No. R01 HL078785-01). The U.S. government may have certain rights to this invention.

BACKGROUND OF THE INVENTION

Oxidative stress induced by reactive oxygen species (ROS) including $H_2O_2$ produced by leukocytes and vascular cells plays a key role in pathogenesis of many disease conditions including atherosclerosis, stroke, hypertension, inflammation, Acute Lung Injury (ALI/ARDS), thrombosis, ischemia-reperfusion injury, organ transplantation, diabetes, angina and myocardial infarction. Therefore, containment of vascular oxidative stress is important to prophylaxis and treatment of these maladies.

Small antioxidants and scavengers can attenuate oxidative stress by terminating lipid peroxidation chain reactions and repairing oxidized molecules in the body, yet they are consumed in these reactions and, therefore, are protective only at very high concentrations. Also, they poorly detoxify directly toxic ROS. Antioxidant inducers, i.e., agents that boost production of natural antioxidants and antioxidant enzymes in the body, also work only at large doses and require pro-longed treatment to develop protective effects. Therefore, while these antioxidant agents may have some utility for alleviating subtle chronic oxidative stress (for example used in form of dietary additions), they have little, if any value for protection against severe acute insults.

In contrast, antioxidant enzymes (e.g., catalase and superoxide dismutase), are not consumed in reactions with ROS, directly detoxify ROS (this preventing the very initiation of oxidative reactions) and are very effective even at very low doses. Therefore, antioxidant enzymes can afford more potent protection, which is critically important for containment of acute and sub-acute severe oxidative stress, such as that occurring in inflammation, stroke, infarction or ALI/ARDS. However, inadequate delivery to endothelial cells lining vascular lumen has hampered their effectiveness for treatment of these and other pathological conditions involving vascular oxidative stress (Muzykantov (2001) J. Control. Rel. 71:1-21).

In order to improve delivery to endothelium, representing both a source of ROS and a critically important, vulnerable target of oxidants (Springer (1990) Scand. J. Immunol. 32:211-216; Varani, et al. (1990) Shock 2:311-319; Heffner & Repine (1989) Am. Rev. Respir. Dis 140: 531-554), diverse means of delivery have been designed (Kozower, et al. (2003) Nat. Biotechnol. 21:392-398; McCord (2002) Methods Enzymol. 349:331-341). For example, targeting of catalase conjugated with antibodies against endothelial cell adhesion molecules ICAM-1 and PECAM-1 boosts vascular antioxidant defense and alleviates oxidative stress in cell cultures (Muzykantov, et al. (1999) Proc. Natl. Acad. Sci. USA 96:2379-2384; Sweitzer, et al. (2003) Free Radic. Biol. Med. 23:1035-1046), perfused organs (Atochina, et al. (1998) Am. J. Physiol. 275:L806-L817), lung transplantation in rats (Kozower, et al. (2003) supra) and lung injury in mice (Christofidou-Solomidou, et al. (2003) Am. J. Physiol. 285:L283-L292). In addition to enhanced delivery of therapeutics, targeting cell adhesion molecules inhibits leukocyte adhesion to the endothelium, thus attenuating their pro-inflammatory functions (DeMeester, et al. (1996) Transplantation 62:1477-1485; Lefer, et al. (1996) Am. J. Physiol. 270:H88-H98; Kumasaka, et al. (1996) J. Clin. Invest. 97:2362-2369)

Studies have revealed that enzymes targeted to endothelial cells (including ICAM-1 and PECAM-1 directed conjugates) enter endothelial cells via a novel internalization mechanism, cell adhesion molecule-mediated endocytosis (Muro et al. (2003) J. Cell. Sci. 116:1599-1609), which provides a pathway for intracellular drug delivery of sub-micron drug-loaded carriers targeted to ICAM-1 or PECAM-1 (Wiewrodt, et al. (2002) Blood 99: 912-922). This enhances detoxification of injurious diffusible intracellular oxidants and minimizes catalase shedding from cell surface (Muro et al. (2003) supra) Using a model polystyrene nanoparticle system with surface-absorbed catalase, it was found that the subsequent intracellular trafficking led to a lysosomal destination and degradation of catalase within 3 hours after delivery, restricting the duration of antioxidant protection (Muro, et al. (2003) Am. J. Physiol. Cell Physiol. 285: C133 9-C134 7). Moreover, other nanoparticle systems are suggested for encapsulation of proteins (see, e.g./U.S. Pat. Nos. 5,543,158 and 6,007,845); however, loading protocols for maintaining functional activity of cargo enzymes are lacking.

Accordingly, there is a need in the art for a delivery system for targeting active therapeutic enzymes and other therapeutic proteins to cells which provides protection of the proteins from subsequent cellular degradation. The present invention meets this need in the art. Furthermore, it establishes a novel class of drug delivery systems based on polymer nanocarriers loaded with encapsulated active enzymes that are not only protected against proteolysis, but capable of carrying out their therapeutic function in the body and inside the target cells without need for drug release from the carrier, due to detoxification of toxic compounds (e.g., ROS) diffusing through the polymer carriers.

SUMMARY OF THE INVENTION

The present invention is a method for producing a polymeric nanocarrier-encapsulated protein composition resistant to protease degradation. The method involves the steps of homogenizing at least one protein and an organic polymer solution at subzero temperature so that an emulsion is formed, mixing the emulsion with an aqueous phase, and homogenizing the mixture to produce a polymeric nanocarrier-encapsulated protein composition. Certain embodiments of the invention provide for encapsulation of antioxidant enzymes and enzymes involved in the detoxification of xenobiotics. In other embodiments, an affinity moiety is conjugated to the surface of the nanocarrier. In still other embodiments, that the polymer is selected for pH-dependent degradation.

Polymeric nanocarrier-encapsulated protein compositions are also encompassed by the present invention for use in in vivo and in vitro methods for decomposing a reactive oxygen species, protecting against vascular oxidative stress, and detoxifying xenobiotics.

DETAILED DESCRIPTION OF THE INVENTION

The present invention is a nanocarrier system for administration of therapeutic proteins. It has now been found that homogenization of proteins with an organic polymer solution at subzero temperatures, and subsequent homogenization in an aqueous phase, encapsulates the protein within the polymer with concurrent preservation of protein structure and activity thereby increasing the therapeutic efficacy of the protein. In contrast to standard double emulsion conditions at 4° C., which yield 2% loading of proteins into polymeric nanoparticles, subzero homogenization enhances loading by 10-fold. Not wishing to be bound by theory, it is believed that by incorporating a freeze thaw cycle during polymeric nanocarrier synthesis, the polymer phase precipitates around the primary emulsion, improving overall encapsulation. This is supported by the observation that at higher polymer concentrations (>100 mg/mL) the freeze-thaw cycle results in the complete precipitation of the polymer phase.

A protein, as used in the context of the present invention refers to a molecule composed of amino acids joined by peptide linkages. Included within the term protein are structural proteins such as albumins, globulins, histones, collagens, elastins, and keratins; and proteins with a chemical function to fulfill, e.g., enzymes. Also included are protein molecules united with nonprotein molecules to produce compound proteins such as nucleoproteins, mucoproteins, lipoproteins and metalloproteins. A protein of the invention can be naturally-occurring, synthetic or semi-synthetic.

Functionally active proteins that are particularly useful for encapsulation in the instant polymeric nanocarrier include clinically relevant proteases and their inhibitors such as serpins (Schimmoller, et al. (2002) Curr. Pharm. Des. 8:2521-31; Rosenblum & Kozarich (2003) Curr. Opin. Chem. Biol. 7:496-504; Barnes & Hansel (2003) Lancet 364:985-96); growth factors and hormones (Bremer, et 5 al. (1997) Pharm. Biotechnol. 10:239-54; Rosier, et al. (1998) Clin. Orthop. 8294-300; Chen & Mooney (2003) Pharm. Res. 20:1103-12; Peppas, et al. (2004) Expert Opin. Biol. Ther. 4: 881-7); enzymes, e.g., for replacement therapies (Layer, et al. (2001) Curr. Gastroenterol. Rep. 3: 101-8; Meikle & Hopwood (2003) Eur. J. Pediatr. 162(Suppl 1): S34-7; Mignani & Cagnoli (2004) J. Nephrol. 17:354-63); anticoagulants and fibrinolytic plasminogen activators (Harker, et al. (1997) Thromb. Haemost. 78:736-41; Wieland, et al. (2003) Curr. Opin. Investig. Drugs 4:264-71); Interferons and cytokines (Burke (1999) Cytokines Cell. Mol. Ther. 5:51-61; Younes & Amsden (2002) J. Pharm. Sci. 91:2-17; Barnes (2003) Cytokine Growth Factor Rev. 14:511-22); as well as an antibodies, antibody fragments and their conjugates with toxins and other biologically active agents (Foster (1996) J. Allergy Clin. Immunol. 98:S270-7; Muzykantov (2001) J. Control. Rel. 71:1-21; Thorpe (2004) Clin. Cancer Res. 10:415-27).

In one embodiment, the polymeric nanocarrier-encapsulated protein is an antioxidant enzyme which is capable of reducing oxidative damage by decomposing or degrading reactive oxygen species. Antioxidant enzymes particularly useful include: catalase, glutathione peroxidase, superoxide dismutase, hemeoxygenase, glutathione-S-transferase, or synthetic or mimetic enzymes thereof. An antioxidant enzyme encapsulated in the instant polymeric nanocarrier is particularly useful in methods for detoxifying reactive oxygen species including the superoxide anion radical ($O_2.^-$), hydrogen peroxide ($H_2O_2$), hypochlorous acid (HOCl), hydroxyl radical (OH.), and singlet oxygen ($^1O_2$) which are generated in the body, mediating cell damage and apoptosis. When the instant polymeric nanocarrier contains an antioxidant enzyme and an affinity moiety for targeting vascular endothelial cells, sustained therapy against vascular oxidative stress can be achieved for the prevention or treatment of pathological processes involved in disease conditions including atherosclerosis, hypertension, diabetes, stroke, myocardial infarction, acute lung injury, inflammation and ischemia-reperfusion injury.

In another embodiment, the polymeric nanocarrier-encapsulated protein is an enzyme which detoxifies one or more xenobiotics. In accordance with its classical definition, a xenobiotic is defined as a compound or molecule which is foreign to the body or a living organism. As such, a xenobiotic is intended to include insecticides, elicit drugs, pharmaceutical agents, organic chemicals, chemical warfare agents, toxins (including endotoxins), and the like which can have an adverse effect on a subject, Enzymes which detoxify xenobiotics can be used to reduce, inhibit, or ameliorate the effects of an intentional or unintentional exposure (including overdosing) to one or more xenobiotics. Moreover, detoxifying enzymes can be provided to subjects with impaired liver function, e.g. due to alcoholism, fatty liver disease, biliary cirrhosis, and hepatocarinomas leading to lower detoxification activity in general (Lee (1995) N. Engl. J. Med. 333: 1118-1127); or suffering from a peroxisomal disorder such as hyperoxaluria, Refsum disease, and β-Oxidation disorders. Xenobiotic detoxifying enzymes particularly suitable for encapsulation in the instant polymeric nanocarrier include, but are not limited to, cytochrome P450 enzymes such as Cyp3A4 and Cyp3A5, Cyp1A1, Cyp1A2, Cyp2D6, Cyp2E1, Cyp2C, Cyp2C9, Cyp2B6, Cyp2C19 and the like which are responsible for the metabolism of a variety of drugs including cyclosporin, nifedipine, warfarin, phenacetin, caffeine, aflatoxin B1, ethanol, carbon tetrachloride, coumarin, sparteine, cyclophosfamide, etc. (Iarbovici (1997) J. NIH Res. 9:34-45; Benet, et al. (1996) In: The Pharmacological $9^{th}$ Basis of Therapeutics, Molinoff, et al. (eds.), $9^{th}$ edition new York, N.Y.: McGraw-Hill, pp 3-27; Verneulen (1996) In: Cytochrome P450: Metabolic and Toxicological Aspects, Ioannides, ed., Boca Raton, Fla.: CRC Press, Inc. pp 29-53); alcohol dehydrogenase; epoxide hydrolase; glucuronyl transferases (detoxifying phenols, thiols, amines, and carboxylic acids); sulfotransferase (detoxifying phenols, thiols, and amines); N- and O-methyl transferases (detoxifying phenols and amines); N-acetyl transferase (detoxifying amines); and other peroxisomal enzymes including peroxidases, catalase, phytanoyl-CoA hydroxylase, and α-methylacyl-CoA racemase. In cases where the xenobiotic is of an unknown origin, it is contemplated that a polymeric nanoparticle containing a plurality of detoxifying enzymes can be employed to facilitate detoxification of the unknown agent.

Accordingly, while particular embodiments of the present invention embrace the encapsulation of at least one protein in a polymeric nanocarrier of the invention, other embodiments provide that at least two, three, four, five, or more types of proteins are encapsulated in the instant polymeric nanocarrier.

Advantageously, the proteins encapsulated in the instant polymeric nanocarriers can exert their effect without release from the polymeric nanocarriers. Therefore, in particular embodiments of the present invention, the protein encapsulated in the instant polymeric nanocarrier composition is not released from the polymeric nanocarrier during the course of use due to direct diffusion of substrates (such as toxic compounds including ROS) through the polymeric matrix of the carrier and decomposition within the nanocarrier. In other embodiments, however, gradual degradation of the polymer carrier (e.g., in a pH-dependent manner) can be used for controlled-release of encapsulated cargo(s) thereby regulating the extent and duration of the activity of the cargo.

In accordance with the instant method, the protein and an organic polymer solution are homogenized to form an emulsion. Homogenization is intended to mean a mechanical process for reducing the size of an organic polymer particle of an emulsion to uniform size. Homogenization steps can be carried out using any conventional ultrasound or homogenizer in accordance with the teachings disclosed herein, wherein rate and time of homogenization can vary depending upon the polymeric nanocarrier characteristics desired. Particularly suitable homogenization parameters for the first homogenization step of the instant method include a rate in the range of 5 to 20 krpm, or more desirably 9 to 16 krpm, for less than one minute. Particularly suitable homogenization parameters for the second homogenization step of the instant method include a rate of homogenization in the range of 5 to 20 krpm, or more desirably at least 15 krpm, for less than one, two, three or four minutes. Alternatively, pressurized homogenization strategies can be used in conjunction with the freeze-thaw encapsulation process.

While a standard double-emulsion method carried out at 4° C. provides 2% loading of a protein In a polymeric nanocarrier, particular embodiments of the present invention embrace carrying out the first homogenization step of the instant method at subzero temperature. As used herein, subzero temperature is intended to encompass a temperature in the range of −180° C. to 0° C. In particular embodiments, subzero temperatures are in the range of −40° C. to −100° C. The particular temperature selected can be dependent upon the melting point of the solvent used and the protein being encapsulated. For example, a subzero temperature of greater than −97° C. is desired when dichloromethane is used. Similarly, temperatures greater than −67° C., −87° C., −78° C. or −97° C. should be used when chloroform, ethyl acetate, butyl acetate, or acetone solvents are respectively employed.

A solvent of the present invention is used for suspending the instant polymer in solution, wherein the particular solvent selected can be an aqueous solvent or an organic solvent. Suitable solvents of the present invention include alkylated alcohols, ethers, acetone, alkanes, dimethyl sulfoxide, toluene, cyclic hydrocarbons, benzene, and the like.

The term polymer or polymeric refers to molecules formed from the chemical union of two or more repeating units. Accordingly, included within the term polymer may be, for example, dimers, trimers and oligomers. The polymer can be synthetic, naturally-occurring or semi-synthetic. In a particular form, polymer refers to molecules which are 10 or more repeating units.

In certain embodiments, the organic polymer of the present invention is biodegradable. In other embodiments the organic polymer is a block copolymer, i.e., a combination of two or more chains of constitutionally or configurationally different features. Block copolymers include diblock, triblock, or multiblock copolymers. Examples of biocompatible organic polymers suitable for use in block copolymers of the present invention are poly (ethylene-covinyl acetate), and silicone rubber cross-linked to poly (dimethyl siloxan sulfoxide) and derivatives thereof, polylactic acid, polyglycolic acid or polycaprolactone and their associated copolymers, e.g., poly(lactide-co-glycolide) at all lactide to glycolide ratios, and both L-lactide or D, L-lactide. In particular embodiments, a poly (lactic-co-glycolic) acid (PLGA) is employed. Amphiphilic diblock copolymers composed of hydrophilic blocks, e.g., including polypyrrolidone, poly(amino acids), polyether, polysaccharide or polyacrylic acid and its hydrophilic ester derivatives; and hydrophobic blocks, e.g., polyanhydrides, polydioxanones, polyphosphazenes, polyesters, polylactones, polyfumarates, polymers of alpha-hydroxy carboxylic acids, polyhydroxybutyric acid, polyorthoesters, polycaprolactone, polyphosphates, or copolymers prepared from the monomers of these polymers can be used to form copolymers for use in preparing the instant nanocarriers. In one embodiment, the hydrophilic block of the copolymer exists as an ester end-capped form. In another embodiment, the hydrophilic block of the copolymer exists in its native form providing linkage sites for an affinity moiety. In certain embodiments, the hydrophilic domain of the block copolymer has a molecular weight in the range of 100 to 20000 Daltons. In other embodiments, the hydrophobic domain of the block copolymer has a molecular weight in the range of 2000 to 300000 Daltons. In particular embodiments, the weight fraction of hydrophilic domain does not exceed 75 weight % of the polymer content. The variety of materials that can be used to prepare the block copolymers forming the nanocarriers significantly increases the diversity of protein retention time within the nanocarrier and degradation profile that can be accomplished in vivo.

Degradation of the hydrophobic-block of the copolymers occurs through a hydrolytic reaction that is acid/base catalyzed. Based on the assays disclosed herein, nanocarrier lifespans are greatly reduced under acidic conditions, but can be predetermined by blending large and small molecular weight fractions of the diblock copolymer. Due to this accelerated rate and the a priori knowledge of lysosomal pH (pH 4.5-5.5), the instant nanocarriers can be designed to have pH-dependent degradation such that their degradation time in the lysosomal compartments can be regulated to a desirable rate thereby facilitating release of a drug, its longevity in the target cells, and rate of metabolization of the whole nanocarrier.

The block copolymers of the present invention are desirably composed of a polymeric-backbone having functional (e.g., pendant side chain or endcapped) groups for physically cross-linking with other entities, including affinity moieties, therapeutic entities, or other polymers. Functional groups encompass conjugatable groups such as amines, hydroxyls, carbonyls, thiols, and carboxylic acids for covalently bonding of other bioactive molecules to the surface of the polymeric nanocarrier. The linkages formed following conjugation of the bioactive molecules to the conjugatable groups include amides, esters, and thioethers. Examples of polymers which have conjugatable functional groups include (poly)lysine, acetylated poly(lysine), poly (glutamic acid), and polyethylene glycol (PEG) and the like. In particular embodiments, a block copolymer of the present invention contains polyethylene glycol (PEG). Generally PEG polymers for use herein have a molecular weight of from about 1000 to about 7500, or more suitably with molecular weights of from about 3000 to about 6000.

The emulsion (i.e., mixture of two or more generally immiscible liquids) produced after the first homogenization step of the instant method is subsequently mixed with an aqueous phase at a temperature of 4° C. to 25° C. and subjected to a second homogenization to generate the instant polymeric nanocarrier. A suitable aqueous phase can include water, saline and the like. In particular embodiments the aqueous phase contains a surfactant. A surfactant refers to a substance that alters energy relationship at interfaces (e.g., that of organic polymers displaying surface activity) and generally encompasses wetting agents, detergents, penetrants, spreaders, dispersing agents, and foaming agents. Surfactants can be of natural, semi-synthetic (modified natural) or synthetic origin. Exemplary natural polymers include naturally occurring polysaccharides and proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, polyethylenes including PLURONIC® compounds, polypropylenes, polyurethanes such as polyvinyl alcohol and polyvinylpyrrolidone, and polyamides including polylactic acids. Methods for preparing polymeric nanocarriers which employ surfactants will be readily apparent to those skilled in the art, in view of the present disclosure, when coupled with information known in the art (e.g., U.S. Pat. No. 5,205,290).

In particular embodiments, the instant nanocarrier further contains an affinity moiety. An affinity moiety refers to any material or substance which can promote targeting of the compositions of the present invention to particular cells, tissues and/or receptors in vivo or in vitro. The affinity moiety can be synthetic, semi-synthetic, or naturally-occurring. Materials or substances which can serve as affinity moieties include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, bioactive agents, and genetic material, including nucleosides, nucleotides, nucleotide acid constructs and polynucleotides. Particularly suitable affinity moieties include molecules which specifically bind to receptors or antigens found on vascular cells. Other suitable affinity moieties target endothelial receptors, tissues or other targets accessible through a body fluid or receptors or other targets upregulated in a tissue or cell adjacent to or in a bodily fluid. For example, affinity moieties attached to nanocarriers designed to deliver proteins to the eye can be injected into the vitreous, choroid; or sclera; affinity moieties attached to nanocarriers designed to deliver proteins to the joint can be injected into the synovial fluid; or affinity moieties to the spine and brain can be delivered into the cerebral spinal fluid.

The affinity moiety can have other effects, including therapeutic effects, in addition to specifically binding to a target. For example, the affinity moiety can modulate the function of an enzyme target. By modulating cellular function, the affinity moiety is meant to alter/enhance cellular response when compared to not adding the affinity moiety. In most cases, a desired form of modulation of function is inhibition. Examples of affinity moieties which can have other functions or effects include agents such as Combrestastatin A4 Prodrug (CA4P) which can be used as a vascular affinity moiety that also acts as an anti-angiogenesis agent; and Cidecin, a cyclic lipopeptide, used as a bactericidal and anti-inflammatory agent.

Exemplary affinity moieties attached to the polymeric nanocarrier of the present invention include, but are not limited to, peptides such as RGD-containing peptides (e.g. those described in U.S. Pat. No. 5,866,540); bombesin or gastrin-releasing peptide; antibodies such as anti-PECAM; and peptides designed de novo to be complementary to tumor-expressed receptors, antigenic determinants, or other receptor targeting groups. These affinity moieties can be used to control the biodistribution, non-specific adhesion, and blood pool half-life of the polymeric nanocarrier compositions. In particular embodiments, the affinity moiety is attached by covalent means. In another embodiment, the attachment is by non-covalent means. For example, antibody affinity moieties can be attached by a biotin-avidin biotinylated antibody sandwich to allow a variety of commercially available biotinylated antibodies to be used on the coated polymeric nanocarrier. In other embodiments, the affinity moiety is added in a single step, e.g., through the coupling of biotinylated nanocarriers and antibody-streptavidin chemical conjugate or fusion construct.

The size of the instant nanocarrier can be adjusted for the particular intended end use including, for example, environmental detoxification or therapeutic use. As the size, feed ratio, and homogenization conditions of polymer can be readily manipulated, the overall size of the nanocarrier can be adapted for optimum passage of the nanocarrier through the permeable vasculature at the site of pathology, as long as the agent retains sufficient size to maintain its desired properties (e.g., circulation life-time). Accordingly, the nanocarriers of the present invention can be sized at any given diameter within the interval between 20 and 20,000 nm as desired. In addition, the size of the nanocarrier can be chosen so as to permit a first administration of nanocarrier of a size that cannot pass through the permeable vasculature, followed by one or more additional administrations of nanocarriers of a size that can pass through the permeable vasculature. In connection with particular uses, for example, intravascular use, it may be desirable that the vesicles be no larger than about 500 nm in diameter, with smaller vesicles being most desired. In certain embodiments of the present invention, a polymeric nanocarrier of the present invention has a diameter of less than 1 micron. In other embodiments, a 50 to 900 nm polymeric nanocarrier is produced. In particular embodiments, the polymeric nanocarrier is in the range of approximately (i.e., ±50 nm) 100 nm to 400 nm in diameter.

The present polymeric nanocarrier compositions are desirably formulated in an aqueous environment. Diluents which can be employed to create such an aqueous environment include, for example, normal saline and physiological saline, water, including deionized water or water containing one or more dissolved solutes, such as salts or sugars, which preferably do not interfere with the formation and/or stability of the nanocarrier or their therapeutic use.

To illustrate the preparation and use of the instant polymeric nanocarrier compositions, PEG-PLGA nanocarrier-encapsulated catalase was prepared and used to degrade the reactive oxygen species, hydrogen peroxide. To achieve targeted vascular antioxidant therapy, polymeric nanocarriers can contain functional groups for the surface attachment of affinity moieties such as antibodies to endothelial adhesion molecules (Muzykantov, et al. (1999) supra; Sweitzer, et al. (2003) supra; Atochina, et al. (1998) supra; Christofidou-Solomidou, et al. (2003) supra; DeMeester, et al. (1996) supra). Thus, a PEG moiety was selected for facilitating surface attachment (Mercadal, et al. (2000) Biochim. Biophys. Acta 1509:299-310; Maruyama, et al. (1997) Adv. Drug Deliv. Rev. 24:235-242; Olivier, et al. (2002) Pharm. Res. 19:1137-1143). In addition, external PEG chains impart stealth properties to polymeric nanocarriers (Mosqueira, et al. (2001) Pharma. Res. 18:1411-1419; Photos, et al. (2003) J. Control Rel. 90:323-334). Conjugation was carried out using copolymers of 38 kD PLGA and 10 kD PEG with an unblocked terminal hydroxyl group. PEG and lactic acid assays showed that the polymer contained 11 weight 5% PEG (50% conjugation yield). Gel permeation chromatography confirmed that the molecular weight was 50,000 with a polydispersity index (PDI) of 2.03. Fourier transform infrared spectroscopy (FTIR) analysis verified presence of both the carbon hydrogen stretch of PEG saturated backbone at 2850 $CM^{-1}$ and the ester peak of the PLGA at 1790 $CM^{-1}$ in the copolymer.

To demonstrate that catalase, residing inside the nanocarrier, could degrade $H_2O_2$ which permeates across the nanocarrier barrier, the diffusivity of hydrogen peroxide through PLGA was measured. Because diffusivity is a bulk property it is insensitive to geometry. Thus, a classical two-chamber polymer-film diffusion study was employed. From these experiments, it was demonstrated that $H_2O_2$ could easily diffuse through the PLGA polymer (film thickness varied from 80 to 200 μm). Under the experimental conditions, steady-state and a constant driving force was assumed. The following equation (1), derived from Fick's first law of diffusion, was used to calculate the film permeability (Bell & Peppas (1996) Biomaterials 17:1203-1218).

$$\ln\left(1 - \frac{2C_t}{C_0}\right) = -\frac{2A}{V}\frac{Dk}{1}t \quad (1)$$

where A is the area of the diffusion plane, V is the volume of the receptor cell, D the diffusivity, k the partition coefficient, 1 the thickness of the polymer film, $C_0$ the concentration of the donor cell and $C_t$ the calculated cumulative concentration of the receptor cell at time, t. Averaging data of two PLGA films with three replicates each, diffusivity of $H_2O_2$ through PLGA was found to be $3.3\pm0.37\times10^{-7}$ CM²/s. While diffusion of $H_2O_2$ through PLGA polymer was slower than in water, the rate was 10 times faster than with lipid membranes (Seaver & Imlay (2001) J. Bacteriol. 183:7182-7189).

The synthesis of polymeric nanoparticles consisting of PEG-PLGA and other biodegradable polymers provides examples of polymeric nanoparticle loading with small soluble drugs resistant to harsh conditions of polymeric nanoparticle formulation (Avgoustakis, et al. (2002) J. Control. Rel. 79:123 135; Suh, et al. (1998) J. Biomed. Mater. Res. 42:331-338; DeCampos, et al. (2001) Int. J. Pharma. 25 224: 159-168) However, loading of enzymes into a polymeric matrix under such harsh conditions usually inactivates the enzymes. For example, a probe sonication, double emulsion followed by rapid solvent evaporation employed for encapsulation of L-aspariginase and interferon-alpha impaired the activity of both proteins (Sanchez, et al. (2003) Eur. J. Pharm. Sci. 18:221-229; Gaspar, et al. (1998) J. Control. Rel. 52:53-62). Loading of protein C (a60-kD monomer serine protease that cleaves coagulation factors) into mPEG-PLGA polymeric nanoparticles using a similar probe sonication approach using an acetone/DCM mixture caused protein C inactivation, yet a fraction of released protein C could be recovered (Zambaux, et al. (2001) Int. J. Pharm. 212; 1-9).

Likewise, in the presence of DCM, catalase activity was reduced by 80% after a 10 second of sonication, while the acetone/DCM (50:50) co-solvent mixture actually exacerbated inactivation, with 60% activity loss even without sonication (Table 1). These data indicate low endurance of large multimeric enzymes to loading, which likely depends on complex cargo quaternary structure (catalase is a 240-kD tetramer containing central coordinated heme redox group). Since this sonication-induced deactivation was not observed in a pure aqueous system, an interfacial-mediated unfolding of catalase is the likely mechanism of deactivation.

To load catalase into PEG-PLGA matrix during polymeric nanocarrier formation without loss of enzymatic activity, a double emulsion-solvent evaporation method (Avgoustakis, et al. (2002) supra; Zambaux, et al. (2001) Int. J. Pharm. 212:1-9), employing either ultrasound or mechanical homogenization for emulsification, was used. When the latter approach was employed, catalase retained 90% activity after 1 minute 15000 RPM homogenization in acetone/DCM at 4° C. and ~60% when a −80° C. freeze-thaw cycle was included. Since mechanical emulsification produces particles with a wide size-distribution, serial centrifugations and filtration through a one-micron filter were employed to isolate the polymeric nanocarrier fraction (particles <700 nm diameter) from larger microparticles. Double emulsion polymeric nanocarriers possess both an inner and external aqueous phase, resulting in an enhanced energy penalty that makes the loading of aqueous drug inside polymeric nanocarrier pockets unlikely. Since entropy works against loading, conceivably the polymeric nanocarrier loading is not determined by equilibrium partition of the drug into the polymeric nanocarrier, but rather by the kinetic effects of polymer gelation that reduces the inner aqueous domain release into the outer aqueous compartment. As such, standard loading conditions resulted in poor loading (2.25%±0.82% of $^{125}$I-catalase). However, when polymer precipitation/gelation was induced by a freeze-thaw cycle in the primary emulsion step, catalase loading into the polymeric nanocarrier fraction was enhanced to a loading efficiency of 13.5%±2.95%.

As particle size decreases, the interface between the oil and water phase increase. To initially overcome the energy barrier, energy (e.g., mechanical homogenization) is added to the system. However, once energy input is ceased, the oil phase starts to coalesce into increasingly larger sizes unless enough surfactant is present to stabilize the system, or the polymer solidifies prior to coalescence. This hardening of the polymer phase is controlled predominately by the solvent evaporation rate (a kinetic parameter) but is also determined by the polymer molecular weight and intrinsic features of the solvent. In agreement with this, size of the polymeric nanocarriers decreased with increasing energy input in the secondary emulsion down to a minimum size determined by the surfactant load of the system (Table 2).

TABLE 2

| 2nd Homogenization | Size (nm ± SE) | |
|---|---|---|
| Rate (krpm) | 11 Weight % PEG | 5 Weight % PEG |
| 5 | 292.6 ± 7.3 | 733.3 ± 111.0 |
| 10 | 277.8 ± 13.7 | 497.2 ± 72.4 |
| 13.5 | 270.7 ± 13.1 | 534.2 ± 92.7 |
| 15 | 256 ± 5.8 | 367.2 ± 40.0 |
| 20 | — | 359.5 ± 20.0 |

Determining polymeric nanocarrier size as a function of rate²/time, a scaling factor for energy input, illustrates this effect (Table 3).

TABLE 1

| | Percent Activity Remaining | | | |
|---|---|---|---|---|
| | Homogenization (20 krpm) | | Sonication (20 W) | |
| Time (seconds) | DCM without Freezing | DCM at −80° C. | DCM | Acetone/ DCM |
| 0 | 100 ± 8.73 | 90.10 ± 9.92 | 100.00 ± 13.00 | 37.91 ± 4.41 |
| 5 | — | — | 63.75 ± 16.28 | 51.04 ± 7.82 |
| 10 | 80.21 ± 10.16 | 61.64 ± 6.72 | 22.61 ± 6.57 | 28.11 ± 2.80 |
| 20 | — | — | 15.29 ± 11.27 | 1.85 ± 1.08 |
| 30 | 104.71 ± 8.66 | 44.20 ± 4.73 | — | — |
| 60 | 87.84 ± 8.30 | 56.46 ± 8.28 | — | — |

TABLE 3

| Energy Input | Size (nm ± SE) | |
|---|---|---|
| (krpm² * time) | 11 Weight % PEG | 5 Weight % PEG |
| 25 | 326.6 ± 16.0 | 692.3 ± 98.3 |
| 100 | 309.0 ± 17.8 | 545.3 ± 46.2 |
| 112.5 | 319.8 ± 9.7 | — |
| 182.25 | — | 547.6 ± 46.5 |

TABLE 3-continued

| Energy Input | Size (nm ± SE) | |
|---|---|---|
| (krpm$^2$ * time) | 11 Weight % PEG | 5 Weight % PEG |
| 225 | 297.6 ± 7.3 | 416.6 ± 31.1 |
| 400 | 291.4 ± 9.9 | 300.2 ± 8.9 |
| 1125 | 280.6 ± 10.1 | — |

The average polymeric nanocarrier size decreased with an increase in homogenization rate and time (Table 2, Table 4).

TABLE 4

| 2nd Homogenization Time (Minutes) | Size (nm ± SE) |
|---|---|
| 0.5 | 337.2 ± 14.9 |
| 1.0 | 275.6 ± 32.2 |
| 2.0 | 291.4 ± 17.1 |
| 5.0 | 280.6 ± 17.6 |

Polymeric nanocarriers decreased in size from 350 to 250 nm as the homogenization rate increased from 5 to 20 krpm. When the PEG content in the PEG-PLGA was decreased from 11 to 5 weight %, the size dependence became even more evident, varying from 700 to 350 nm. To analyze significant number of samples and estimate reproducibility, dynamic light scattering measurements were used to determine polymeric nanocarrier size in most experiments. Electron microscopy confirmed size of polymeric nanocarriers determined by dynamic light scattering.

To assess the role of surfactant stabilization in polymeric nanocarrier synthesis, the effect of PVA surfactant was analyzed for PEG-PLGA polymeric nanocarriers with 5 weight % PEG. As PVA concentration increased (from 0.1 to 4 weight %) the size of the polymeric nanocarrier increased for both second homogenization rates tested, 15 and 20 krpm (Table 5). For each equivalent PVA concentration, the polymeric nanocarrier formed at 20 krpm was smaller than the 15 krpm counterpart (Table 5).

TABLE 5

| PVA Concentration | Particle Size (nm ± SE) | |
|---|---|---|
| (weight %) | 15 krpm | 20 krpm |
| 0.1 | 296.0 ± 8.5 | 267.8 ± 2.4 |
| 1.0 | 295.4 ± 3.4 | 277.2 ± 6.9 |
| 2.0 | 320.9 ± 6.6 | 302.4 ± 4.7 |
| 4.0 | 372.0 ± 41.8 | 359.5 ± 20.0 |

Increased surfactant concentration also increased the 25 polymeric nanocarrier yield (5 to 25 weight %; Table 6).

TABLE 6

| PVA Concentration (weight %) | Nanoparticle yield (% ± SE) |
|---|---|
| 0.1 | 4.3 ± 1.2 |
| 1.0 | 6.2 ± 1.9 |
| 2.0 | 10.8 ± 1.5 |
| 4.0 | 24.7 ± 9.9 |

The interfacial area of the oil-to-water phase was defined by the following equation (2):

$$IA = C_{particles} \cdot SA_{particles} = \frac{3 C_{mass}}{\rho r} \quad (2)$$

where $C_{particles}$ is the number concentration of polymeric nanocarrier, $SA_{particle}$ is the surface area of the polymeric nanocarrier, $C_{mass}$ is the mass concentration of the particles, $\rho$ is the polymer density (assumed to be 1.2 g/cm$^3$), and r is the mean particle radius. This analysis showed an overall increase in oil/water surface area per volume of emulsion (Table 7).

TABLE 7

| PVA Concentration (weight %) | Interfacial Area/Volume Emulsion (1/cm ± SE) |
|---|---|
| 0.1 | 18.7 ± 1.9 |
| 1.0 | 16.0 ± 5.1 |
| 2.0 | 41.6 ± 3.5 |
| 4.0 | 80.1 ± 15.8 |

Results of chemical assays of the conjugated diblock PEG-PLGA confirmed the conjugation efficiency to be 50%. This result represents a relatively under-appreciated aspect of polymeric nanocarrier synthesis, i.e. r role of diblock PEG-PLGA to monoblock PLGA feed ratio. The majority of polymeric nanocarrier prepared herein was synthesized using either PEG-PLGA in its pure form or mixed with bulk PLGA. It was found that the diblock PEG-PLGA to monoblock PLGA feed ratio represented a significant factor that controls size of the resultant polymer particles (Table 8).

TABLE 8

| | PEG-PLA (constant weight % PEG) | | Constant PEG-PLGA (10 mg/ml) + PLGA | |
|---|---|---|---|---|
| PEG-PLGA Concentration (mg/ml) | Particle Size (nm ± SE) | Interfacial Area/Volume Emulsion (1/cm ± SE) | Particle Size (nm ± SE) | Interfacial Area/Volume Emulsion (1/cm ± SE) |
| 5 | 412.3 ± 8.7 | 6.5 ± 0.7 | — | — |
| 10 | 349.7 ± 4.6 | 9.2 ± 1.3 | 422.0 ± 36.6 | 12.1 ± 3.5 |
| 25 | 306.5 ± 7.9 | 21.2 ± 1.7 | 467.2 ± 59.7 | 14.5 ± 2.0 |
| 50 | 280.0 ± 14.9 | 21.7 ± 2.4 | 563.2 ± 22.5 | 16.9 ± 4.8 |
| 100 | 263.5 ± 6.5 | 54.0 ± 2.0 | 692.3 ± 106.8 | 5.0 ± 0.7 |

Increases in PEG-PLGA diblock content decreased the subsequent polymeric nanocarrier size, possibly due to the surfactant qualities afforded by this amphiphile. This is further substantiated by the fact that increasing polymer concentration with a constant weight % of PEG (5 weight %) resulted in a decrease in polymeric nanocarrier size (from 400 to 250 nm) and an increase in polymeric nanocarrier yield (from 1 to 5 mg). In contrast, when the polymer concentration was increased with a constant 10 mg/mL PEG-PLGA concentration, particle size increased from 400 to 700 nm and the interfacial area per volume remained relatively constant. Moreover, increases in PEG-PLGA concentration increased yield (Table 9). The measured PEG content of the polymeric nanocarrier matched that of the feed conditions, confirming that PEG-PLGA did not preferentially self-associate into micelle structures and polymeric nanocarrier polymer composition can be predetermined by simply altering the copolymer mixtures.

TABLE 9

| PEG-PLGA Concentration (mg/ml) | Nanocarrier Yield (% ± SE) |
|---|---|
| 5 | 0.8 ± 0.1 |
| 10 | 1.0 ± 0.1 |
| 25 | 2.1 ± 0.1 |
| 50 | 1.8 ± 0.2 |
| 100 | 4.3 ± 0.1 |

The activity of loaded catalase was determined by the direct monitoring $A_{242\,nm}$ absorbance of $H_2O_2$ that is relatively stable in water in minute time scale. The addition of unloaded polymeric nanocarrier elevated a net absorbance due to light scattering, but produced no measurable subsequent decrease in $H_2O_2$. In a sharp contrast, catalase-loaded polymeric nanocarriers produced the same increase In absorbance that was immediately followed by a decrease in $H_2O_2$ absorbance, compatible to the kinetics of a similar amount of free catalase. Therefore, catalase loaded into polymeric nanocarriers retained its enzymatic activity and effectively decomposed $H_2O_2$ diffusing through the polymer shell.

Increases in the rate of homogenization in the primary emulsion (up to 20 krpm) did not alter catalase activity, but a primary homogenization time extending beyond 1 minute at 15 krpm inactivated catalase-loaded polymeric nanocarrier (Table 10). Because the first emulsion homogenization has limited effect on polymeric nanocarrier size, a 1-minute homogenization is sufficient for the effective synthesis of polymeric nanocarrier in the size range of interest.

TABLE 10

| Time (minutes) | Enzyme Activity (Units/mg polymeric nanocarrier ± SE) |
|---|---|
| 0.25 | 3.3 ± 0.4 |
| 0.75 | 3.2 ± 1.8 |
| 2.00 | 0.1 ± 0.1 |
| 5.00 | 0.06 ± 0.04 |

Loading of catalase into the primary emulsion without versus with a freeze-thaw cycle endowed the polymeric nanocarriers with marginal versus substantial catalase activity, respectively, under the secondary homogenization rates analyzed (Table 11). This was in correlation with $^{125}$I-catalase loading data.

TABLE 11

| 2nd Homogenization Speed (krpm) | Enzyme Activity (Units/mg polymeric nanocarrier ± SE) | |
|---|---|---|
| | Freeze-Thaw | No Freeze-Thaw |
| 5.0 | 0.97 ± 0.06 | 0.09 ± 0.07 |
| 10.0 | 2.07 ± 0.87 | 0.13 ± 0.04 |
| 13.5 | — | 0.19 ± 0.07 |
| 15.0 | 2.50 ± 0.74 | 0.12 ± 0.06 |
| 20.0 | 1.29 ± 0.28 | — |

Second emulsion homogenization times longer than one minute also deteriorated catalase activity (0.91±0.36 U/mg polymeric nanocarrier with 1-minute homogenization versus 0.42±0.06 U/mg polymeric nanocarrier with 5 minutes homogenization). The homogenization rate of the second emulsion displayed a bell-shape optimum of catalase-loaded polymeric nanocarrier activity (~15 krpm) followed by reduction at 20 krpm.

Supporting this result, $^{125}$I-catalase loading into polymeric nanocarrier was >20% versus <5% at 15 krpm versus 25 krpm, respectively, in second emulsion. Unexpectedly, at the polymer concentration used (25 mg/mL), the loading efficiency was independent of polymer composition and molecular weight (Table 12). Thus, polymer molecular weight and composition can be used to control polymeric such as degradation rate, sizing, and in vivo circulation.

TABLE 12

| Polymer | Size | Loading Efficiency (% ± SE) | |
|---|---|---|---|
| | | 15 krpm | 25 krpm |
| mPEG-PLA | 50 kDa | 12.8 ± 2.1 | 4.6 ± 2.4 |
| | 30 kDa | 21.9 ± 7.1 | 4.2 ± 3.3 |
| | 20 kDa | 15.2 ± 6.5 | 4.3 ± 4.0 |
| PEG-PLGA | 50 kDa | 13.5 ± 5.2 | 2.4 ± 1.7 |

In addition to compositional analysis, it was determined whether nanocarriers protect loaded catalase from proteolysis. After a 4-hour incubation with PRONASE® free catalase possessed <1% of initial $H_2O_2$-degrading activity, while catalase-loaded polymeric nanocarrier retained 35% of initial activity. Co-incubation of catalase with unloaded polymeric nanocarrier did not protect catalase from PRONASE®, indicating that only catalase encapsulated into polymeric nanocarriers is protected against proteolysis and therefore capable of degrading $H_2O_2$ diffusing through the polymer shell. The time-course of the proteolytic loss of catalase activity was also determined (Table 13). About 90% of free catalase activity was lost after 1-hour incubation, and fell below measurable levels at 6 hours. In contrast, catalase loaded into the disclosed polymeric nanocarrier formulation retained 40% of its initial activity at 6 hours. The activity seemed to reach a plateau with 25% of the initial activity remaining at stable level for at least ~20 hours. The loss of activity in the polymeric nanocarrier was believed to be associated with the catalase that was either surface bound or was released into the aqueous medium. However, the stable, active fraction represents catalase residing inside the protease inaccessible domains of the polymeric nanocarrier. When the catalase was loaded into polymeric nanocarriers formed using a 20% aqueous content in the primary emulsion (instead of the 10 weight % employed through these studies), initial rate of loss of catalase was significantly accelerated. However, after 1 hour, the activity stabilized at level of ~25% of initial activity.

TABLE 13

| Time (hours) | Remaining Activity (% ± SD) | |
|---|---|---|
| | Catalase-loaded Nanocarrier | Free Catalase |
| 0.0 | 100.0 ± 0.0 | 100.0 ± 0.0 |
| 0.5 | 83.4 ± 8.4 | 25.3 ± 0.2 |
| 1.0 | 91.7 ± 11.8 | 18.6 ± 3.9 |
| 2.0 | 65.6 ± 6.1 | 7.0 ± 2.8 |
| 4.0 | 48.5 ± 4.4 | 3.7 ± 1.5 |
| 6.0 | 39.8 ± 6.0 | 2.6 ± 1.3 |
| 22.0 | 24.8 ± 8.3 | 1.2 ± 0.6 |

To illustrate targeting of a polymeric nanocarrier of the present invention to a particular cell type, anti-PECAM-1 antibodies were conjugated to the surface of the polymeric nanocarrier utilizing a PEG-tethered biotin-streptavidin linkage (Wu & Pardridge (1999) Proc. Natl. Acad. Sci. USA 96(1):254-9; (Hansen, et al. (1995) Biochim. Biophys. Acta 1239 (2):133-44). Amine-terminated diblock PEG-PLGA copolymers were synthesized using an art-established direct conjugation procedure, providing 90% conjugation efficiency as determined by $^1$H-NMR. The tertiary amine catalyst was not necessary, since a primary amine PEG was used. NHS-Biotin reacted in anhydrous conditions resulted in conjugation onto the primary amine end of PEG, as determined by FTIR, which presented the carbonyl stretch of the urea bond (1630 cm$^{-1}$) in biotin.

To avoid aggregation, antibody-streptavidin conjugates were employed. Streptavidin was modified with the heterobifunctional cross-linker succinimidyl 4-[N-maleimidomethyl]cyclohexane-1-carboxylate (SMCC) to introduce maleimide groups, while SH-groups were introduced onto the antibody molecule using N-succinimidyl-S-acetylthioacetate (SATA). As such, an antibody was linked to streptavidin, forming anti-PECAM-streptavidin or IgG-streptavidin. Introducing one sulfhydryl per IgG molecule prevented multivalent cross-linking and aggregation.

Single emulsion-polymeric nanocarriers were covered with 130 antibodies/polymeric nanocarrier which is 55% of the theoretical maximum IgG coverage. With an increase in size (double emulsion-polymeric nanocarrier, 420 nm), 1200 antibodies/polymeric nanocarrier could be achieved, which is 30% of the theoretical maximum. This result may be due to the internal voids contained within polymeric nanocarriers and therefore less biotin is available for surface coverage; or due to the lower radius of curvature which reduces the surface accessibility of the relatively large streptavidin-IgG conjugate.

Coupling capacity of polymeric nanocarriers was analyzed using the modular IgG-streptavidin in combination with structurally uniform solid core nanoparticles (solid-polymeric nanocarriers) of PEG-PLGA with and without 15 mol % biotin-PEG-PLGA. $^{125}$I-IgG-streptavidin conjugates bound specifically to biotin-containing polymeric nanocarrier (177.5±9 IgGs/polymeric nanocarrier), but not biotin-free polymeric nanocarriers (3.0±0.1 IgGs/polymeric nanocarrier). This translates into a 33.5±1.7% of maximum coverage (assuming the 8000 antibodies/µm$^2$ maximum coverage for pure polystyrene beads). With subsequent centrifugations, there was no measurable antibody on the surface of the polymeric nanocarrier without biotin and the biotin-polymeric nanocarrier contained a significant fraction of the initially bound amount. The biotin labeled polymeric nanocarrier lost a small fraction of radiolabel with each centrifugation step. However, the noticeable decrease in pellet size with each centrifugation is indicative of a decrease in particle loss rather than detachment of antibody conjugate. Further, biotin-polymeric nanocarrier readily resuspended without significant aggregation. The initial size of the polymeric nanocarrier preparations was 120 nm, yet with centrifugation and resuspension, both polymeric nanocarriers with (169.6±12 nm) and without biotin (143±3 nm) exhibited a size increase. The difference in size (Δ26 nm) of these preparations was only slightly larger than the expected increase in size as a result of antibody coating (assuming a $r_h$ of ~10 nm). This difference may be a result in the larger size of the antibody streptavidin-conjugate compared to unconjugated IgG.

Double emulsion nanocarrier-encapsulated catalase was also synthesized with 15 mol % biotin-PEG-PLGA. $^{125}$I-IgG-20 streptavidin, but not control $^{125}$I-IgG (i.e., streptavidin-free) coated the nanocarrier containing catalase with a high yield (1245±64 versus 46±34, respectively). Thus, total amount of IgG per nanocarrier containing catalase was higher than that for solid-polymeric nanocarrier, likely due to the larger size (~420 nm versus 120 nm) of the nanocarrier containing catalase. However, surface coating of IgG was 28±1.4% of the theoretical max, confirming the general nature of this modular coupling strategy.

Polymeric nanocarrier binding to cells expressing PECAM was tested in vitro. As a control for both cell specificity and adhesion specificity, blank and anti-PECAM-single emulsion-polymeric nanocarrier were incubated (340 pM) for 1 hour with REN and REN/PECAM cells to visualize polymeric nanocarrier binding. Anti-CAM targeting of latex beads results in localization at cell-cell borders (for anti-PECAM) and perinuclear regions as a result of internalization (Muro, et al. (2003) J. Cell Sci. 116(Pt 8): 1599-609). A similar pattern of localization was found with the anti-PECAM/polymeric nanocarrier incubated with REN/PECAM, indicating that single emulsion-polymeric nanocarriers are capable of being internalized by REN/PECAM cells. PECAM-single emulsion-polymeric nanocarriers bound specifically to the REN/PECAM cells (117±11 polymeric nanocarriers/cell), compared to wild-type REN cells (17.56±2 polymeric nanocarriers/cell). Pure PEG-PLGA polymeric nanocarrier possessed little to no binding to both REN/PECAM (2.2±0.5 polymeric nanocarriers/cell) and wild-type REN cells (0.0±0.0 polymeric nanocarriers/cell).

To obtain a more quantitative analysis of binding, polymeric nanocarriers were partially labeled (5 mole % of total surface coated conjugate) with a nonspecific $^{125}$I-IgG-streptavidin. Particle binding was traced in an endothelial cell line (HUVEC) with IgG-streptavidin-coated polymeric nanocarrier as a control. It was found that anti-PECAM particle binding was dose-dependant with (193±1.5 polymeric nanocarriers/cell) at a polymeric nanocarrier concentration of 29 µM. When repeated with double emulsion-polymeric nanocarrier, binding was (330±101 polymeric nanocarrier/cell) at 22 pM. Due to the high standard deviation of the double emulsion results, there was not a statistically significant difference between the single emulsion and double emulsion polymeric nanocarriers. In both experiments, IgG coated particles possessed little binding (15±3.5 and 15±0.7 polymeric nanocarriers/cell for single emulsion and double emulsion formulations, respectively) These values are in close agreement with latex bead studies, which have shown maximum binding to be ~250 polymeric nanocarriers/cell for 100 nm beads. Further, there appeared to be maximum binding of polymeric nanocarrier reached for the double emulsion-polymeric nanocarrier but not for the single emulsion-polymeric nanocarrier. This was likely a result of the greater size of the double emulsion-polymeric nanocarrier versus single emulsion-polymeric nanocarrier, where it has been demonstrated that efficiency of CAM targeting of submicron particles is distinctly size-dependant.

Toxicity, circulation and targeting in vivo were also performed. $^{125}$I-catalase-loaded polymeric nanocarriers (composed purely of functionalized PEG-PLGA) were administered via i.v. to mice and rats with no detectable pathological changes in the animals. Approximately 70% of the injected dose of free catalase was cleared within 10 minutes, in agreement with published data (Muzykantov, et al. (1996) Proc. Natl. Acad. Sci. USA 93(11):5213-8). In contrast, catalase-loaded polymeric nanocarrier circulated for a dramatically longer time in both rats and mice, with at least 60% of the injected dose present at 3 hours. The initial, more rapid, clearance of catalase-loaded polymeric nanocarrier during the first 30 minutes may have been due to heterogeneities in polymeric nanocarrier size which occur during formulation, altered vasoreactivity in response to blood withdraw, or loss of surface bound fraction of catalase. The secondary clearance phase had a projected half-life of 12 hours. Organ distribution was typical for sub-500 nm polymeric nanocarriers. Liver and spleen displayed major uptake of polymeric nanocarrier containing catalase (although a significant fraction of catalase could be associated with the residual blood in these highly perfused organs) There was no significant pulmonary uptake of polymeric nanocarrier containing catalase, indicating lack of intravascular aggregation and sequestration in the capillaries. Lack of non-specific or mechanical (embolization) pulmonary uptake was useful as a low baseline for targeting toward this vascular bed.

During the course of this analysis, more than one preparation of polymeric nanocarrier was employed. Plotting of the cumulative data collected 1-hour post-injection revealed dependence of blood circulation on polymeric nanocarrier size. Even within a relatively narrow range of 200-350 nm, circulation was reduced with increase in size. Therefore, modulation of polymeric nanocarrier size may provide for optimization of delivery and treatment design.

In similar in vivo analyses carried out with nanocarriers coated with anti-PECAM as an affinity moiety, ~10% of the injected targeted polymeric nanocarrier loaded with catalase was found in the lungs versus 1% of the non-targeted catalase-loaded polymeric nanoparticles at 1 hour after injection in mice. Furthermore, the blood distribution was markedly reduced. Lung/blood ratio for anti-PECAM/polymeric nanocarrier-catalase versus non-targeted polymeric nanocarrier containing catalase was 2.7 versus 0.24, respectively. Thus, the ratio of lung uptake for targeted versus non-targeted polymeric nanocarrier containing catalase normalized per blood level was above 10.

Hydrogen peroxide injury studies were performed to evaluate the therapeutic potential of the anti-PECAM-targeted polymeric nanocarriers. Release of $^{51}CrO_4$ from pre-labeled cells was used as a marker of cellular necrosis. Percent protection was defined by the following equation (3), $$P = 100 - 100 * \frac{(Cr - Cr_0)}{(Cr_+ - Cr_0)} \quad (3)$$

Where P is percent protection, Cr is the chromium release of the sample, $Cr_0$ is the chromium release of uninjured ($H_2O_2$ null) cells and $Cr_+$ is the chromium release of unprotected $H_2O_2$ injured cells.

For polymeric nanocarrier-protein-based therapy, a sufficient amount of active protein must be loaded and delivered to the site of injury to exert a benefit. In protection studies based upon $^{125}$I-catalase tracing of catalase loaded polymeric nanocarriers, protection correlated with delivered mass of drug (19.2±10.5% and 56.9±2.9% protection for 7.0±1.5 and 32±4.4 ng catalase/well, respectively). This result demonstrated that even when relatively low amount of protein was delivered, a marginal amount of cellular protection was possible. When, carriers were targeted, a greater amount of polymeric nanocarrier was present and protection increased in response. Due to the small size of polymeric nanocarriers, and therefore limited cargo capacity, initial activity of the loaded catalase greatly influenced the protection capabilities of the delivery system, with 56.9±2.9% and 100±8.6% protection for the 30 kU/mg- and 55 kU/mg-loaded catalase, respectively.

Using 55 kU/mg catalase-loaded polymeric nanocarriers, anti-PECAM-polymeric nanocarriers were pre-incubated for set times prior to injury to test the duration of therapeutic protection. Hydrogen peroxide concentration in the supernatant was measured to directly monitor delivered catalase activity. From this monitoring of $H_2O_2$ degradation and cellular protection, it was found that catalase loaded into targeted polymeric nanocarriers was active and protected cells for times much longer than previously observed (up to 21 hours). While little visible change was noted in the first three hours, there was a statistically significant difference between concentrations of $H_2O_2$ at 5 minutes. To track changes in effectiveness of catalase activity, a first order degradation model was fitted to each curve, where the time constant is equivalent to the total activity in the well. Normalizing this residual activity with the initial values, a loss of catalytic activity as a function of time was obtained. For pure protein conjugates (e.g., as described by Sweitzer, et al. (2003) supra; Kozower, et al. (2003) supra and Christofidou-Solomidou, et al. (2003) supra), activity was almost completely lost by 2-3 hours of incubation with cells. Unexpectedly, the loss of delivered catalase activity mirrored the slow loss of activity in catalase-loaded polymeric nanocarriers observed under artificial proteolytic conditions as disclosed herein. This result indicates that the rate-limiting step in the loss of activity of catalase delivered to the cells may be controlled by the polymeric nanocarrier, and therefore loss could be determined by varying the properties of the delivering vehicle.

When catalase-loaded polymeric nanocarriers were incubated with cells for less than 3 hours (where activity was decreased by 30%) prior to insult, enough active catalase was present to degrade 100% of the hydrogen peroxide in 10 minutes, translating into 100% cellular protection for the first three hours. Further, catalase-loaded polymeric nanocarriers incubated with cells for 24 hours possessed a stable 20% of its initial catalase activity, which was capable of detoxifying hydrogen peroxide in 50 minutes, resulting in 56.7±8.7% protection. This level of delivery and capacity to protect against strong oxidizing conditions indicates an unprecedented window of protection from a single, targeted catalase dose. The overall protection potency (defined by the actual % protection divided by the 1 hour protection level), decreased at a slower rate than the actual loss of catalase activity. This result demonstrates that when a sufficient amount of catalase is present, a decoupling of protection from enzyme loss is possible, thereby providing even greater activity durations than what would be otherwise possible. For instance, by adding twice as much needed catalase for protection, 100% can be achieved for 8 hours (activity half-life ~4 hours), while for pure protein conjugates such a load would only provide protection for <1 hour.

Therefore, targeted delivery of detoxifying enzymes encapsulated into a small molecule-permeable polymer carrier of sub-micron size affords protection against damage from toxic small molecules for a duration of time which has not been achieved by a single bolus of unencapsulated enzyme. Thus, detoxifying enzymes in polymeric nanocarriers, which do not release the enzyme cargo, provides prolonged therapeutic action intracellularly for use in methods for decreasing vascular oxidative stress and detoxifying xenobiotics.

Accordingly, the present invention is a method for decomposing a reactive oxygen species (ROS) using a polymeric nanocarrier-encapsulated antioxidant enzyme. The method involves contacting a sample containing a ROS with the nanocarrier-encapsulated antioxidant enzyme so that decomposition of ROS to non-toxic low levels is achieved. A sample is intended to include, a biological sample (e.g., an organ for transplantation), as well as an environmental sample or laboratory sample. For example, storage of organs for re-implantation is severely limited by the ROS generated upon reperfusion of the transplanted organ. The ROS stress generated from reperfusion is proportional to the time of ischemia (storage time) inflicted upon the organ. By injecting the donors before, or infusing organs immediately after the harvest with antioxidant nanocarriers, the "shelf-life of the organ can be greatly extended, increasing the number of patients that can receive transplants. Moreover, it is contemplated that a nanocarrier-encapsulated antioxidant enzyme could be used to scavenge ROS in chemical synthesis reactions.

Local administration of antioxidant enzymes or antioxidant enzyme-encoding genes, as well as antioxidant enzyme overexpression by transgene technologies, has been shown to protect against oxidative stress in animal models (Fridovich (1995) Annu. Rev. Biochem. 64:97-112; Erzurum, et al. (1993) J. Appl. Physiol. 75(3):1256-62). However, containment of vascular oxidative stress using exogenous antioxidant enzymes requires extended activity of the enzyme because the majority of pathological conditions involving vascular stress take time ranging from days to weeks (e.g., inflammation, acute lung injury, stroke, hyperoxia, myocardial infarction and post-ischemic syndrome) and months to years (e.g. atherosclerosis, hypertension, diabetes) Thus, delivery of an antioxidant enzyme in a polymeric nanocarrier as disclosed herein provides prolonged therapeutic effect due to protection from proteolysis. Moreover, when the instant polymeric nanocarrier contains an antioxidant enzyme and an affinity moiety for targeting vascular endothelial cells (e.g., anti-PECAM or anti-ICAM), an increase in efficacy of reducing vascular oxidative stress at vascular epithelium can be achieved. To effect protection against vascular oxidative stress, a subject in need of treatment (e.g.; having pathological conditions which induce production of toxic oxidants) is administered an effective amount of a polymeric nanocarrier-encapsulated antioxidant composition of the present invention. Such treatment desirably provides a detectable decrease (i.e., detectable by either chemical methods documenting reduction of ROS levels or by biological outcomes such as survival or extent of organ damage) in the vascular oxidative stress in the subject.

Administration of the instant antioxidant enzyme compositions can be prior to medical procedures (e.g.; surgery or radiation treatment) that are known to cause ROS generation, thereby preventing the onset of vascular oxidative stress and improving patient recovery, reducing recovery time and hospitalization costs. Alternatively, administration of the nanocarrier-encapsulated antioxidant enzyme can be as in intervention in debilitating situations such as acute lung injury, sepsis (toxic shock), autoimmune diseases, etc., thereby limiting the progressive damage caused by ROS under these extreme oxidative stress situations.

Differing administration vehicles, dosages, and routes of administration can be determined for optimal administration of the instant nanocarrier compositions; for example, injection near the site of an injury or tumor may be preferable for facilitating local treatment. For example, biodegradable nanocarriers composed of PLGA with anti-inflammatory (e.g., hydrocortisone) and growth factors (e.g., BDNF) encapsulated therein can be administered via direct lumbar injection using a standard spinal tap procedure. Nanocarriers introduced into the cerebral spinal fluid are dispersed through this space via natural convective motion and accumulate at the wound site as a result of the enhanced permeation and retention (EPR) effect (Torchilin (2000) Eur. J. Pharm. Sci. 11 (Suppl. 2): S81-91). Also, targeting can be further enhanced by the inclusion antibodies toward common inflammatory markers.

Generally, the nanocarrier compositions used in the invention are administered to an animal in an effective amount. Generally, an effective amount is an amount of encapsulated protein effective to either reduce the symptoms of the disease sought to be treated or induce a pharmacological change relevant to treating the disease sought to be treated. Therapeutically effective amounts of the encapsulated proteins can be any amount or doses sufficient to bring about the desired effect and depend, in part, on the condition, type and location of the pathology, the size and condition of the patient, as well as other factors readily known to those skilled in the art. The dosages can be given as a single dose, or as several doses, for example, divided over the course of several weeks.

The polymeric nanocarrier compositions of the instant invention can be administered by any suitable means, including, e.g., parenteral, topical, oral or local administration, such as by injection (e.g., into the vasculature) or by aerosol (e.g., into the lungs). In certain embodiments, administration is by injection. Such injection can be locally administered to any affected area. For particular modes of delivery, a polymeric nanocarrier composition of the instant invention can be formulated with an excipient. See, e.g., Remington: The Science and Practice of Pharmacy, Alfonso R. Gennaro, editor, 20th ed. Lippincott Williams & Wilkins: Philadelphia, Pa., 2000. Routes of administration of targeted polymeric nanocarriers can be by intravenous, interperitoneal, or subcutaneous injection including administration to veins or the lymphatic system. While the primary focus of the invention is on vascular-targeted nanocarriers, in principle, a targeted nanocarrier can be designed to focus on markers present in other fluids, body tissues, and body cavities, e.g., synovial fluid, ocular fluid, or spinal fluid. Thus, for example, a nanocarrier can be administered to spinal fluid, where an antibody targets a site of pathology accessible from the spinal fluid. Intrathecal delivery, that is, administration into the cerebrospinal fluid bathing the spinal cord and brain, may be appropriate for example, in the case of a target residing in the choroid plexus endothelium of the cerebral spinal fluid (CSF)-blood barrier. Polymeric nanocarrier compositions can be administered to any animal, desirably to mammals, and more desirably to humans.

In addition to ROS, the instant invention embraces the detoxification of xenobiotics. As disclosed herein, xenobiotics encompass a variety of agents which can be detoxified by, e.g., peroxisomal enzymes. Xenobiotic detoxification can be carried out in vivo or in vitro. As such, one method of the present invention involves contacting a sample containing a xenobiotic with a polymeric nanocarrier-encapsulated detoxifying enzyme composition so that the xenobiotic is detoxified. In the context of this method, a sample can be of biological or environmental origin, or any other source contaminated with a xenobiotic. For example, it is contemplated that a polymeric nanocarrier-encapsulated dehalogenase could find application in environmental remediation.

In accordance with in vivo applications, a polymeric nanocarrier-encapsulated detoxifying enzyme is administered to a subject exposed to a xenobiotic in amount which effectively detoxifies the xenobiotic. Generally, an effective amount is an amount of encapsulated protein effective to either reduce the symptoms associated with the xenobiotic or detoxify the xenobiotic present in the subject to less toxic or non-toxic levels. For example, by injecting the instant nanocarrier composition into the vascular endothelium, which is directly exposed to circulating toxins, xenobiotics can be rapidly degraded (oxidized) into more inert, water-soluble forms, allowing for a more rapid recovery time. Such a strategy would allow for a benign and more generically applicable first treatment of unknown or antidote-lacking toxins and allow for prophylaxis of at risk populations (e.g., accidental industrial chemical release or military personnel in a chemical warfare setting).

As will be appreciated by the skilled artisan, in addition to loading large proteins (e.g., catalase having a molecular weight of 240 kD), the instant method of preparing polymeric nanocarriers can be used for loading small to middle-size proteins without enzymatic activity (e.g., insulin or albumin) or other molecules which are sensitive to shear-induced deactivation during polymer emulsification (e.g., nucleic acids, carbohydrates, organic compounds, etc). The invention is described in greater detail by the following non-limiting examples.

EXAMPLE 1

Materials

All reagents were used as received unless indicated otherwise. Methoxypoly(ethylene glycol) molecular weight 5000 (mPEG) was purchased from Polysciences (Warrington, Pa.). Poly (lactic-co-glycolic acid) (50:50) in the free acid (38,000 molecular weight) form was purchased from ALKERMES®, Inc. (Cincinnati, Ohio) Bovine liver catalase (242,000 Dalton) was obtained from CALBIOCHEM® (EMD Biosciences, San Diego, Calif.). 10-acetyl 3,7-dihydroxyphenoxazine (AMPLEX® Red) and ALEXA FLOUR®-488 goat anti-mouse antibodies were purchased from MOLECULAR PROBES™ (Eugene, Oreg.). Succinimidyl 4-[N-maleimidomethyl]cyclohexane-1-carboxylate (SMCC); N-succinimidyl-S-acetylthioacetate (SATA); and N-succinimidyl-biotin (NHS-biotin) were obtained from Pierce Biotechnology (Rockford, Ill.). $Na^{125}$ and $Cr^{51}$ were purchased from PERKINELMER™ (Boston, Mass.). All other reagents and solvents were obtained from Sigma-Aldrich (St. Louis, Mo.).

EXAMPLE 2

Synthesis of Diblock Copolymers

Diblock copolymers were prepared by three different methods.

PEG-PLGA. PLGA (50:50) polymer containing a carboxylate end group and PEG (10,000 molecular weight) was freeze-dried overnight to remove bound water. The polymers were mixed in a 4:1 molar ratio (PEG/PLGA 38 kDa) in anhydrous dichloromethane (DCM) to a final polymer concentration of 10 weight 9%. Subsequently, 2,2-dicyclocarbodiimide (DCC) and N,N'-dimethylaminopyridine (DMAP) were added to the PLGA at the molar ratio of 4:1:2. Conjugation was carried out under an $N^2$ atmosphere at room temperature for 18 hours. The resulting dicyclohexylurea precipitate was filtered out and the polymer was precipitated twice in anhydrous ether. The filtrate was dried and dissolved in cold acetone. The insoluble fraction was filtered out and once more precipitated in cold ethanol.

mPEG-PLA. DL-lactide was recrystallized twice in anhydrous ether, and mixed with mPEG in weight ratios predetermining their molecular weight (30 kDa). The bulk material was raised to 140° C. for 2 hours under a reduced nitrogen atmosphere. Subsequently, the temperature was reduced to 120° C., 1 weight % stannous 2-ethyl-hexanoate was added, and the polymerization proceeded for 6 hours. The resulting polymer was dissolved in dichloromethane (DCM), and precipitated twice in cold diethyl ether. The final product was serially dried in a rotovap (Safety Vap 205; Buchi, Switzerland) and a freeze dryer (RCT 60; Jouan, Inc., Winchester, Va.) to remove any residual solvent.

Biotin-PEG-PLGA. PLGA (50:50; 38 kDa) polymer containing a carboxylate end group and PEG-Diamine (10,000 molecular weight) was freeze-dried overnight to remove bound water. The polymers were mixed in a 6:1 molar ratio (PEG:PLGA) in anhydrous DCM to a final polymer concentration of 2 weight %. Subsequently, DCC was added to at the molar ratio of 1.2:1 (DCC: PLGA). Conjugation was carried out under an $N^2$ atmosphere at room temperature for 18 hours. The resulting dicyclohexylurea precipitate was filtered out, and the polymer was precipitated twice in anhydrous ether. The filtrate was then dried, dissolved in acetone and precipitated in deionized water. The precipitate was filtered and freeze-dried. Subsequently, biotin-N'-succinimidyl ester was added (1.2:1 molar ratio) with the polymer in DCM. After 4 hours, the polymer was precipitated twice in ether.

The chemistry of the polymer was verified by FTIR (Nicolet Magna IR560; Thermo Nicolet Corp., Madison, Wis.), gel permeation chromatography (GPC) using 2 serial pLGel Mixed C columns 300×7.5 mm (Polymer Laboratories, Amherst, Mass.) with an Acuflow Series III pump and a Differential Refractometer (Knauer, Berlin, Germany) calibrated using polystyrene standards to evaluate polymer molecular weight and the PDI. Relative PEG content was determined as disclosed herein.

EXAMPLE 3

PEG and PLA Content Determination

A 50µl L aliquot of the concentrated nanocarrier prep was saponified by adding 200 µL of 5 M NaOH and reacting the mixture overnight at 80° C. The solution was neutralized with 200 µL of 5 M HCl. PEG concentration was determined by a calorimetric assay based upon a PEG-Barium Iodide complex. Absorbance of the color product was measured at 550 nm using a microplate reader (Model 2550-UV; BIO-RAD® Labs, Hercules, Calif.) (Sims and Snape (1980) Anal. Biochem. 107: 60-63).

To measure PLA concentration, an enzymatic assay for L-lactic acid was used. 5 µL of sample was added to 45 µL of 50 mM PBS in a microplate well. To this well was added 50 µL of assay buffer. The assay buffer consisted of 2 U/mL horseradish peroxidase, 20 mU lactate oxidase and µg/mL of AMPLEX® Red. After a 10-minute incubation at room temperature, the resorufin product concentration was determined by UV absorbance at 550 nm. Concentrations were measured in triplicate for each individual particle preparation.

EXAMPLE 4

Determination of H20 2 Diffusivity in PLGA

The diffusivity of $H_2O_2$ through PLGA was determined by using a two chamber diffusion apparatus. Polymer films of esterified PLGA (34,000 molecular weight) were prepared via solvent casting procedure. The donor cell contained a 5 mM $H_2O_2$ solution in phosphate-buffered saline (PBS; 50 mM, 7.4 pH), and the receptor cell contained pure PBS buffer. At specific time intervals (15 and 30 minutes), the receptor cell contents were removed and replaced with fresh buffer. The concentration of the $H_2O_2$ in the receptor cell was determined by UV absorbance at 242 nm (Cary 50 UV-Vis; VARIAN® Inc., Palo Alto, Calif.). Diffusivity studies were performed in triplicate for two independently cast polymer films.

EXAMPLE 5

Nanoparticle Synthesis

Two types of polymeric nanocarrier syntheses were employed, non-catalase loadable single-emulsion polymeric nanocarrier, and catalase in a double emulsion polymeric nanocarrier.

Single-Emulsion Polymeric Nanocarrier. PEG-PLGA with and without 15 mol % biotin-PEG-PLGA was dissolved in acetone (10 mg/mL, 2.5 mL). This solution was slowly pipetted into 20 mL PBS under mild agitation. Acetone was removed under vacuum using a dry nitrogen stream. Single-emulsion polymeric nanocarrier was collected by centrifugation at 30,000 g for 30 minutes. The pellet was resuspended in 1 mL of PBS. Stock concentrations were determined according to chemical and enzymatic assay.

Double Emulsion Polymeric Nanocarrier. A primary emulsion was formed by homogenizing at 15 krpm for 1 minute (−80° C., dry ice/acetone bath) a 100 μL aqueous drug solution (1-25 mg/mL catalase in PBS) in a 1 mL organic polymer solution (25 mg/mL PEG-PLGA in DCM or for some applications mPEG-PLA with 15 mol % biotin-PEG-PLA in DCM), using a 7-mm blade homogenizer (Kinematica POLYTRON® 3100 equipped with a PTDA3007/2 generator; Brinkmann Instruments, Westbury, N.Y.). This primary emulsion was immediately pipetted into a secondary aqueous phase (5 mL) containing 2 weight % poly (vinyl alcohol) (PVA; 10,000 molecular weight, 80% hydrolyzed), sodium cholate, or 2 weight % PLURONIC™ (F68) and homogenized at 15 krpm for 1 minute. This second homogenization was added to an additional 10 mL of the same surfactant solution, and stirred overnight at room temperature under mild agitation to remove residual solvent.

To purify the resultant nanoparticles, a serial centrifugation scheme was used. The solution was first centrifuged at 1000 g for 15 minutes to remove the large microparticle/macroaggregate fraction. The supernatant was then centrifuged at 22,000 g for 30 minutes. Nanoparticles were rinsed twice more to remove residual surfactant and unloaded protein. Alternatively, to select for nanocarriers of 100 to 300 nm, nanocarriers were filtered through a 1 μm filter. All preparations were performed in triplicate. Particle sizes were determined by dynamic light scattering (0 PLUS Particle Sizer; Brookhaven Instruments, Holtsville, N.Y.).

EXAMPLE 6

Antibody-Streptavidin Conjugate Preparation

Heterobifunctional cross-linker succinimidyl 4-[N-maleimidomethyl]cyclohexane-1-carboxylate (SMCC) was used to introduce stable maleimide reactive group into streptavidin molecules. The reaction was performed at 40-fold molar excess of SMCC at room temperature for 1 hour. In parallel, sulfhydryls were introduced in the antibody or control IgG through primary amine using N-succinimidyl-5-acetylthioacetate (SATA). The yield of the reaction was about 20%. Thus, to introduce 1 sulfhydryl per IgG molecule, antibody was incubated with 5-fold molar excess of SATA at room temperature for 30 minutes. This extent of modification prevented possible cross-linking of streptavidin and subsequent protein polymerization. Sulfhydryls were deprotected using hydroxylamine and antibody was conjugated with streptavidin at 2:1 IgG to streptavidin molar ratio. At each step unreacted components were removed using Spin Protein Columns (G-25 SEPHADEX™; Roche Applied Science, Indianapolis, Ind.).

EXAMPLE 7

Analysis of Enzymatic Activity

The activity of catalase was determined using a standard catalase assay (Shuvaev, et al. (2004) Methods Mol. Biol. 283: 3-20). Briefly, 900 or 950 μL of a 5 mM $H_2O_2$ solution in PBS (7.4 pH) was added to a quartz cuvette at ambient conditions. A catalase-loaded nanoparticle solution was added to bring the total volume to 1 mL. The concentration of $H_2O_2$ was monitored versus time by measuring the absorbance at 242 nm=(1 Unit 23.0·[Δabsorbance/min]). The activity was measured twice at two different concentrations (50 and 100 μL) for each individual particle preparation.

EXAMPLE 8

Loading Analysis

Loading analysis was indirectly calculated by measuring the $^{125}$I-catalase content in solution pre- and post-centrifugations (n=3). Protein content was determined by radiotracing using a WIZARD® 1470 gamma counter (Wallac Oy, Turku, Finland). Catalase was radiolabeled with $Na^{125}I$ (PERKINELMER™, Boston, Mass.) using the IODOGEN® (Pierce Biotech., Rockford, Ill.) method, and unbound iodine was removed from protein using gel permeation chromatography (Biospin 6 Columns, BIO-RAD® Labs, Hercules, Calif.). Conditions were based upon manufacturer's recommendations.

EXAMPLE 9

Determination of Protection of Enzyme

To evaluate the ability of nanoparticles to protect the activity of loaded enzyme, an in vitro proteolytic assay was employed. In these studies, nanoparticles were incubated at 37° C. in a PBS solution containing 0.2 weight % PRONASE®R, a robust proteolytic enzyme. Aliquots were taken at specific intervals of incubation and measured for either enzymatic activity or protein loading content.

EXAMPLE 10

Cell Culture

Pooled human umbilical vein endothelial cells, HUVEC (CLONETICS®, San Diego, Calif.), were cultured at 37° C., 5% $CO_2$, and 95% relative humidity in supplemented M199 medium (GIBCO BRL™, Grand Island, N.Y.) and used at passage 4-5. Non-endothelial REN cells (human mesothelioma) were maintained in RPMI 1640 medium supplemented with 10% fetal bovine serum (HYCLONE®, Logan, Utah), 2 mM glutamine, 100 U/mL penicillin, and 100 μg/mL streptomycin. REN cells stably transfected with human PECAM (REN/PECAM) cells, which express PECAM-1 at levels and cellular localization similar to those found in human endothelial cells were maintained in the same growth medium supplemented with 0.5 mg/mL G418-sulfate. G418-sulfate was omitted from the medium during experiments. For microscopy studies, cells were seeded onto 12-mm coverslips in 24-well plates. For all other studies, cells were coated directly onto 24-well plates. To ensure attachment, HUVEC cells were seeded only onto gelatinized surfaces.

EXAMPLE 11

Binding Studies

Binding studies were carried out using both radiolabeling and fluorescent microscopy. Fluorescence studies were carried out using REN and REN/PECAM cells mounted onto glass coverslips. Cells were incubated with polymeric nanocarriers (single-emulsion polymeric nanocarrier and anti-PECAM-single-emulsion polymeric nanocarrier) for 1 hour at 37° C. Cells were then washed 5 times with PBS and fixed (2% paraformaldyhde, 15 minutes ambient conditions). Cells were washed and labeled with a green fluorescent antibody. Coverslips were then mounted and imaged. Particle binding was semi-quantitatively determined by image analysis.

For Radiotracing studies, polymeric nanocarriers (IgG-polymeric nanocarrier and anti-PECAM-polymeric nanocarrier) were labeled with $^{125}$I-IgG-streptavidin conjugate (5% of total conjugate surface coating). Cells were incubated for 1 hour at 37° C., washed 5 times, and lysed using 1% TRITON™ X-100 in 1N NaOH. Cell supernatants and lysates were collected and counted to determine extent of binding.

EXAMPLE 12

Protection from Cell Injury by $H_2O_2$

Cellular injury in culture was determined by the specific release of $^{51}CrO_4$. To label the HUVEC cells, $^{51}Cr$ isotope (200,000 cpm/well) was added 24 hours prior to the experiment. The HUVEC were washed and incubated with double emulsion-polymeric nanocarrier (anti-PECAM and IgG labeled) for 1 hour in HUVEC medium. Cells were then washed 5 times with RPMI 1640 without phenol red. $H_2O_2$ (5 mM) was added to the cells and the cells were incubated for 5 hours at 37° C. with 5% $CO_2$. Total radioactivity in the supernatant and in the cell lysates was determined.

At the indicated times, $H_2O_2$ remaining in the supernatant medium was measured by H20rdependent oxidation of o-phenylenediamine (15 mM final concentration) in the presence of horseradish peroxidase (5 μg/mL final concentration) as determined by absorbance at 490 nm in a BIO-RAD® 3550 Microtiter Plate Reader.

Stability of catalase loaded-polymeric nanocarriers was determined by incubating polymeric nanocarriers with cells for various times prior to $H_2O_2$ insult. During the 24 period of $^{51}CrO_4$ incubation, double emulsion-polymeric nanocarrier was introduced into the chromium-containing medium at specific times for 1 hour, the cells were washed 5 times with HUVEC medium, and incubated with chromium-containing medium for the remainder of the 24-hour period. Cells were subsequently washed and injury was assessed as described herein.

What is claimed is:

1. A polymeric carrier-encapsulated protein composition produced by the method comprising:
    (a) homogenizing an aqueous solution of at least one protein, with an amphiphilic polymer in an organic solvent at a first temperature below 0° C. so that a first emulsion is produced;
    (b) homogenizing the first emulsion with an aqueous phase containing a stabilizing surfactant at a temperature of between 4° C. to 25° C.;
    (c) removing the organic solvent; and
    (d) wherein the resulting polymeric carrier composition is of a size between 20 nm-20 microns.
2. The composition of claim 1, wherein the amphiphilic polymer is selected from the group consisting of: polypyrolidone, poly(amino acids), polyether, polysaccharide, polyacrylic acid and its, hydrophilic ester derivatives, polyanhydrides, polydioxanones, polyphosphazenes, polyesters, polylactones, polyfumarates, polymers of alpha-hydroxy carboxylic acids, polyhydroxybutyric acid, polyorthoesters, polycaprolactone, polyphosphates, and copolymers prepared from the monomer of these polymers.
3. The composition of claim 1, wherein the organic solvent is dichlormethane.
4. The composition of claim 1, wherein the surfactant is poly (vinyl alcohol), sodium cholate, or polyoxyethylene-polyoxypropylene block copolymer.
5. The composition of claim 1, wherein the protein is an enzyme.
6. The composition of claim 1, wherein the method further comprises the step of conjugating an affinity moiety to the surface of the polymeric carrier-encapsulated protein composition.
7. The method of claim 1, wherein the polymer is selected for pH dependent degradation.
8. The composition of claim 5, wherein the enzyme is an antioxidant enzyme.
9. The composition of claim 5, wherein the enzyme is a detoxifying enzyme.
10. A method comprising delivering the polymeric carrier-encapsulated enzyme composition of claim 5 to a cell, group of cells, or tissue in a subject.
11. The composition of claim 6, wherein the affinity moiety is an antibody.
12. The composition of claim 8, wherein the antioxidant enzyme is catalase.
13. A method comprising delivering the polymeric carrier-encapsulated detoxifying enzyme composition of claim 9 to a cell, group of cells, or tissue in a subject affected by an elevated level of a toxic compound, to facilitate decomposition of this toxic compound.
14. The method claim 13, wherein the toxic compound is a reactive oxygen species.
15. The method of claim 14, wherein the reactive oxygen species is superoxide anion or hydrogen peroxide.
16. The method of claim 14, wherein the detoxifying enzyme is an antioxidant enzyme.
17. A method for protecting against vascular oxidative stress comprising administering to a subject in need of treatment an effective amount of the polymeric carrier-encapsulated antioxidant enzyme composition of claim 6 so that vascular oxidative stress in the subject is decreased.
18. The method of claim 17, wherein the polymeric carrier-encapsulated protein antioxidant enzyme composition is administered via injection or aerosol.
19. The method of claim 17, where the polymeric carrier-encapsulated antioxidant enzyme composition is administered topically.
20. The method of claim 19, ht rein the reactive oxygen species is hydrogen peroxide.
21. A method for detoxifying a xenobiotic comprising administering to a subject exposed to a xenobiotic an effective amount of the polymeric carrier-encapsulated detoxifying enzyme composition of claim 9 so that the xenobiotic is detoxified.
22. The method of claim 21, where the polymeric carrier-encapsulated protein composition is administered topically.
23. A method comprising delivering to a cell, group of cells or tissue of a subject an effective amount of the polymeric carrier encapsulated catalase composition of claim 12, said amount effective to detoxify a reactive oxygen species generated in vivo.

* * * * *